United States Patent
O'Lenick, Jr. et al.

(10) Patent No.: US 6,762,289 B1
(45) Date of Patent: Jul. 13, 2004

(54) SILICONE FUNCTIONALIZED ALKYL POLYGLUCOSIDE SURFACTANTS

(75) Inventors: Anthony J. O'Lenick, Jr., Dacula, GA (US); Kevin A. O'Lenick, Dacula, GA (US)

(73) Assignee: S. LTech LLC, Dacula, GA (US)

( * ) Notice: Subject to any disclaimer, the term of this patent is extended or adjusted under 35 U.S.C. 154(b) by 10 days.

(21) Appl. No.: 10/642,564

(22) Filed: Aug. 18, 2003

(51) Int. Cl.$^7$ .......................... C07H 15/04; C07H 23/00
(52) U.S. Cl. ........................................ 536/4.1; 536/120
(58) Field of Search .................................. 536/4.1, 120

(56) References Cited

U.S. PATENT DOCUMENTS

| 5,428,142 A | 6/1995 | O'Lenick |
| 5,498,703 A | 3/1996 | O'Lenick |

*Primary Examiner*—James O. Wilson
*Assistant Examiner*—Michael C. Henry

(57) ABSTRACT

The invention relates to a series of polyglycoside derivatives that contain silicone functional groups introduced into the molecule by reaction with the hydroxyl groups present in the starting polyglycoside molecule. The compounds are prepared by reacting epoxy silicones with an alkyl polyglucoside under base catalysis.

17 Claims, No Drawings

SILICONE FUNCTIONALIZED ALKYL POLYGLUCOSIDE SURFACTANTS

FIELD OF THE INVENTION

The present invention relates to a series of polyglycoside derivatives that contain silicone groups introduced into the molecule by reaction with the hydroxyl groups present in the alkyl polyglucoside molecule. The preferred products have more than one water-soluble group per molecule and are made with mild reagents to avoid discoloration and mal odor.

Commercial alkyl polyglycosides generally have a low degree of polymerization of polysaccharide, in the molecule. This results in a molecule that is of limited water solubility. The present invention is aimed at functionalizing the hydrophobic alkyl polyglycoside, by including in the molecule phosphate, sulfate, sulfosuccinate, and carboxylate functionalities. These products have been called "alkyl glycosides, alkyl glycosides, alkyl polyglycosides or alkyl polyglycosides" by many different authors. All refer to the same molecules.

BACKGROUND

Alkyl polyglycosides have been known for many years, having been first synthesized in the early 1900 by Emile Fischer. Despite this, the products were of little commercial interest until much later.

U.S. Pat. No. 4,393,203 issued Jul. 12, 1983 to Mao et al, incorporated herein by reference, disclose that long chain fatty alcohols can be removed from alkyl polysaccharide products in thin film evaporators to achieve fatty alcohol levels of less than about 2% without excessive discoloration of the alkyl polysaccharide. This allowed for a more cosmetically acceptable product to be developed that is more surface active. The presence of the free fatty alcohol in the mixture, allows for a more water-soluble product, by removing the water insoluble alcohol.

One of the most significant patents is U.S. Pat. No. 5,003,057 issued Mar. 26, 1991 to McCurry et al incorporated herein by reference, provides for a process for preparing glycosides from a source of saccharide moiety and an alcohol in the presence of a hydrophobic acid catalyst is provided. An example of such a catalyst is dinonylnaphthalenemonosulfonic acid. The use of such catalysts provides a number of process advantages, which includes the reduced production of polar by-products. Preferred glycosides produced by the process are higher alkyl glycosides useful as surfactants.

U.S. Pat. No. 3,598,865 (Lew) discloses the production of higher alkyl ($C_8$–$C_{25}$) glycosides from a monosaccharide or source thereof and a higher monohydric alcohol in the presence of a latent solvent (lower alcohols) and an acid catalyst selected from the group consisting of sulfuric acid, hydrochloric acid, phosphoric acid, phosphorous acid, toluenesulfonic acid, and boron trifluoride.

U.S. Pat. No. 3,219,656 (Boettner) discloses a process for producing a higher alkyl glycoside by reacting glucose with methanol in the presence of a macroreticular-structured sulfonic acid resin, anhydrous and in the acid form, to produce methyl glycoside which is reacted without isolation with butanol to form butyl glycoside and which in turn is reacted with a higher alcohol to form a surface active higher alkyl glycoside.

U.S. Pat. No. 3,839,319 (Mansfield) discloses a process for producing alkyl glycosides by direct, acid catalyzed reaction of a higher alcohol and a saccharide. The acid catalysts are mineral acids such as hydrochloric and sulfuric, and sulfonic acid exchange resins U.S. Pat. No. 5,428,142 issued Jun. 27, 1995 to O'Lenick a series of silicone glycosides prepared by the reaction of a hydroxy containing dimethicone copolyol with a reducing saccharide, or a source of reducing saccharide, in the presence of a suitable catalyst. These materials contain no alkyl groups, having the silicone portion of the molecule replacing the alkyl group in alkyl polyglucoside. The present invention is aimed at taking an alkyl polyglucoside and in a subsequent step silicone functionalizing it, keeping the critical alkyl group present. The alkyl group has been found to be critical to the desired surfactant properties.

U.S. Pat. No. 5,498,703 to O'Lenick issued Mar. 12, 1996 discloses a series of silicone containing glycosides prepared by the reaction of a silanol with a reducing saccharide, or a source of reducing saccharide, in the presence of a suitable catalyst. These materials have no alkyl group in the molecule, having the silicone portion of the molecule replacing the alkyl group in alkyl polyglucoside. The present invention is aimed at taking the alkyl polyglucoside and in a subsequent step, silicone functionalizing it, keeping the critical alkyl group present. These materials have the silicone portion of the molecule replacing the alkyl group in alkyl polyglucoside. The present invention is aimed at taking the alkyl polyglucoside and silicone functionalizing it, with the critical alkyl group present.

THE INVENTION

The present invention relates to the finding that the reaction of the rather hydrophobic alkyl polyglycosides with the proper reagent results in molecules that have improved water-solubility and substantivity. Consequently they overcome many of the shortcomings of the alkyl polyglycosides itself. It is most interesting that the maximum amount of glycoside units per alkyl group that can be added using known technology is 1.5. This means that the product is a mixture of mono and di functional product. This product has the remaining fatty alcohol stripped off in an evaporative process. The resulting product is about 70% by weight of a product of a d.p. of 1, about 21% by weight of a product of a d.p. of 2, about 7% by weight of a product having a d.p. of 3, and about 2% by weight of a product that has a d.p. of 4.

We have surprisingly learned that taking the alkyl polyglycosides produced in the commercial process, with it's inherent lack of water solubility and reacting it to make silicone functionalized surface-active agents, results in a series of products that are much more usable in many applications. Simply put, alkyl polyglycosides make much better hydrophobic raw materials than finished surface-active agents. When some or all of the many hydroxyl groups are converted into silicone functionalized groups, outstanding more widely applicable surface-active agents result.

SUMMARY OF THE INVENTION

Alkyl polyglycosides are complex products made by the reaction of glucose and fatty alcohol. In dealing with the chemistry one talks about degree of polymerization (the so called "d.p."). In the case of traditional alkyl polyglycosides the d.p. is around 1.4. This means that on average thee is 1.4 units of glucose for each alkyl group. The fact of the matter is that the resulting material is a mixture having an average of 1.4.

The specific structure of the product is hard to ascertain completely since many positional isomers are possible, but two examples of structures are as follows;

Alkyl polyglycosides (d.p. 1)

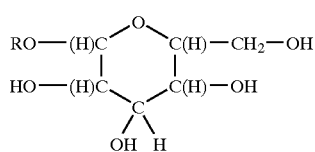

Alkyl polyglycosides (d.p. 2)

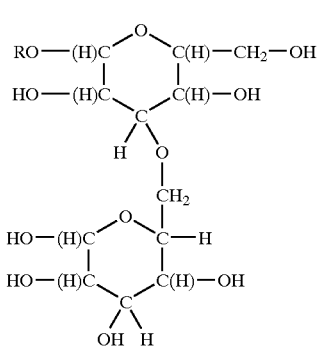

It should be clear that if there is a 50/50 mixture of the d.p. 1 and d.p. 2 product, the resulting analytical data will show that on average there is a d.p. of 1.5. Saying that a molecule has a d.p. of 1.5 does not mean that each molecule has 1.5 glucose units on it.

One key aspects of the present invention relates to the heretofore unappreciated fact that the rather hydrophobic alkyl polyglycosides contain on average five hydroxyl groups, one primary and the other four secondary. The assumption that there is a large degree of group specificity for the primary to react exclusively rather than the four additional hydroxyl groups is simply not true. This means that if on average only one of the five groups is reacted, there remains a very large concentration of reacting alkyl polyglycoside that has no functionality on it. Since the reactant with no functionalization remains water insoluble, there needs to be at lease 2 and as many as 4 hydroxyl groups functionalized to get to the desired water-soluble product. We have observed that when between 2 and 5 groups are reacted, a water-soluble very useful product results. Therefore it is a preferred embodiment having between 2 and 5 of the hydroxyl groups functionalized.

Another key unappreciated fact in making the compounds of the present invention is the selection of the proper reagents to make the desired product. Specifically, if aggressive conditions are used, the starting alkyl polyglycoside discolors and degrades quite seriously, making a large concentration of degradation products that are quite dark, smelly. Reaction of an aqueous alkyl polyglucoside with an epoxy silicone provides a facile method to obtain the desired product.

DETAILED DESCRIPTION OF THE INVENTION

The compositions of the present invention are mixtures conform to the following structures:

(a)

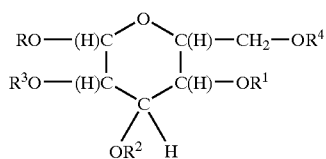

wherein;

R is alkyl having 8 to 22 carbon atoms;

$R^1$, $R^2$, $R^3$, and $R^4$ are independently selected from the group consisting of

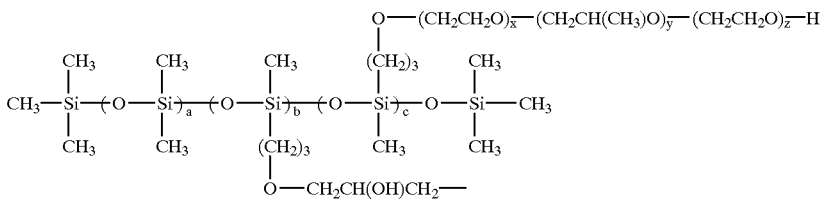

and H, with the proviso that $R^1$, $R^2$, $R^3$, and $R^4$ are not all H;

a is an integer ranging from 0 to 1,000;

b is an integer ranging from 1 to 20;

c is an integer ranging from 0 to 20;

x, y and z are each integers independently ranging from 0 to 20;

and (b)

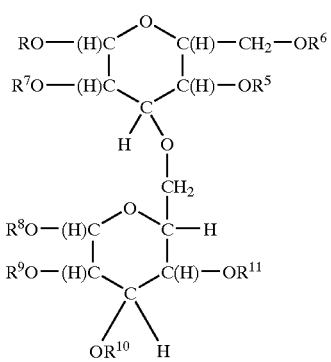

wherein;

R is alkyl having 8 to 22 carbon atoms;

$R^5$, $R^6$, $R^7$, $R^8$; $R^9$ and $R^{10}$ are independently selected from the group consisting of

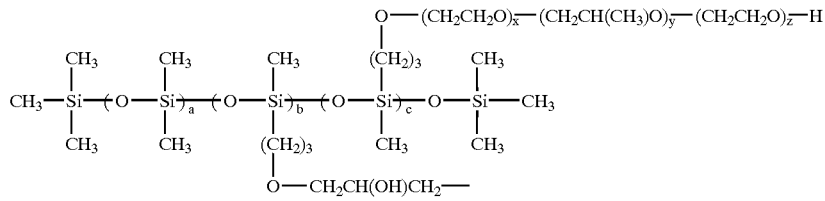

and H, with the proviso that $R^5$, $R^6$, $R^7$, $R^8$, $R^9$ and $R^{10}$ are not all H, a is an integer ranging from 0 to 1,000;

b is an integer ranging from 1 to 20;

c is an integer ranging from 0 to 20;

x, y and z are each integers independently ranging from 0 to 20.

PREFERRED EMBODIMENT

In a preferred embodiment c is 0.

In another preferred embodiment b is 1.

In another preferred embodiment b ranges from 2 to 10.

In another preferred embodiment c ranges from 2 to 10.

In another preferred embodiment R is $C_{12}H_{25}$.

In another preferred embodiment R is $C_{10}H_{21}$.

In another preferred embodiment R is $C_8H_{17}$.

In another preferred embodiment R is $C_{14}H_{27}$.

In another preferred embodiment R is $C_{18}H_{37}$.

In another preferred embodiment R is $C_{18}H_{35}$.

In another preferred embodiment R is $C_{20}H_{42}$.

In another preferred embodiment R is $C_{22}H_{42}$.

In another preferred embodiment a is an integer ranging from 1 to 200.

In another preferred embodiment a is 0.

In another preferred embodiment a is an integer ranging from 10 to 20.

In another preferred embodiment a is an integer ranging from 2 to 5.

EXAMPLES

Preparation of Alkyl Glycosides

Alkyl Glycosides are raw materials used to make the surface-active polyglycoside derivatives of the present invention.

Saccharides useful in the process of making alkyl glycosides are saccharides that can be alkylated in the "1" position, commonly referred to as "reducing saccharides", or higher saccharides that can be hydrolyzed to provide such a saccharide. These saccharides are typically comprised of aldo- or keto-hexoses or pentoses.

Examples of saccharides include glucose (dextrose), fructose, mannose, galactose, talose, allose, altrose, idose, arabinose, xylose, lyxose, and ribose. Examples of hydrolyzable saccharides that are a source of reducing saccharides include starch, maltose, sucrose, lactose, maltotriose, xylobiose, mellibiose, cellobiose, raffinose, stachiose, methyl glycosides, butyl glycosides, levoglucosan, and 1,6-anhydroglucofuranose.

The physical form of the saccharide may vary. The saccharide will typically be in a fluid (as opposed to a solid) state, e.g. as a melt or an aqueous syrup, during at least a portion of the period of reaction, if not for a predominant portion of the period of the reaction. Crystalline (e.g. anhydrous or hydrates) or amorphous saccharide solids in various particle sizes, e.g. granules, powders, etc., can be used, but the heating of the reaction medium may well fluidize at least a portion of a solid reactant, if not a predominant portion of the saccharide reactant. Aqueous syrups of saccharides, typically at saccharide solids of between about 10% and 90% dry solids by weight can also be used. Indeed, the use of the hydrophobic catalysts of this invention should show the most improved results over conventional catalysts in the context of the use of aqueous syrup reactants as compared with processes which employ solid saccharide reactants, particularly with respect to avoiding the formation of deleterious amounts of polysaccharides and very high DP alkyl glycosides during the glycoside formation reaction.

The preferred saccharides are glucose, galactose, xylose and arabinose, or mixtures thereof, for reasons of availability, low cost, and convenience. Glucose in the anhydrous crystalline form is preferred, although dextrose monohydrate, corn syrups of high dry solids (typically 50% to 80% dry solids) and a high dextrose equivalence (D.E.) (typically greater than 90 D.E and most commonly 95 D.E.) can be commonly employed. Indeed, while the higher the purity of the dextrose source, the better the quality of the product (other things being equal), the catalysts of this invention allow the use of a lower purity dextrose source and yet yield a product of substantially equivalent quality as compared with prior catalysts. Because of the ready availability of glucose and its oligomers, much of the remaining description is particularly suited to the use of glucose in its various forms.

Alcohols useful in the process of this invention are hydroxyl-functional organic compounds capable of alkylating a saccharide in the "1" position. The alcohol can be naturally occurring, synthetic, or derived from natural sources and/or derivatized. Examples include monohydric alcohols (more fully discussed below) and polyhydric alcohols (e.g. ethylene glycol, propylene glycol, polyethylene glycols, polypropylene glycols, butylene glycol, glycerol, trimethylolpropane, pentaerythritol, polyester polyols, polyisocyanate polyols, and so on). Other examples include aromatic alcohols such as benzyl alcohol, phenol, substituted phenols (e.g. alkylphenols) and alkoxylates of each.

Preferred alcohols are monohydric alcohols containing from about 1 to about 30 carbon atoms. They may be primary or secondary alcohols, straight or branched chain, saturated or unsaturated (e.g. allyl alcohol, 2-ethylhexenyl alcohol and oleyl alcohol) alkyl or aralkyl alcohols, ether alcohols, cyclic alcohols, or heterocyclic alcohols. In general, these alcohols have minimal solvent power for the saccharide molecule. Examples of the monohydric alcohols which may be employed in the present invention include methyl alcohol, isopropyl alcohol, butyl alcohol, octyl alcohol, nonyl alcohol, decyl alcohol, dodecyl alcohol, tridecyl alcohol, tetradecyl alcohol, pentadecyl alcohol, hexadecyl alcohol, pentacosyl alcohol, oleyl alcohol, linoleyl alcohol, isoborneol alcohol, hydroabietyl alcohol, phenoxyethanol, phenoxypolyethoxyethanol containing five ethoxy groups, 2-methyl-7-ethyl-4-undecanol, and mixtures of one or more of the above.

A preferred group of alcohols are alkanols having the formula ROH wherein R represents an alkyl group having from 8 to 30 carbon atoms. A particularly preferred group of alcohols are those wherein R represents an alkyl radical having from 8 to 20, preferably 11 to 18, carbon atoms. The alkyls can be straight or branched chain.

Alkyl Glycoside Examples

Example 1

A one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 602.4 g (3.105 moles) of a commercial mixture of $C_{11}$ to $C_{15}$ (98% $C_{12}$ and $C_{13}$) straight and branched alkanols (Neodol 23 available form Shell Chemical Co.) and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57.degree. C. and heating was continued until the slurry had reached 110.degree. C. At this time 3.2 g (0.00345 mole of a commercially available mixture of 50% dinonyinaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in $H_2O$) was added. An aliquot of the neutralized reaction mixture (3.39 g, 1 g dissolved substance) was dissolved in a total volume of 10 ml with 1:1 isopropanol:water. The pH of this solution was 7.8.

The remainder of the reaction mixture was evaporated to a clear melt at 200.degree. C. and 1 mm pressure using a Leybold-Heraeus Distact.™. wiped film evaporator operating at a: feed rate of 700 ml/hr.

The residue was analyzed using a combination of gas and liquid chromatographic techniques as well as NMR spectroscopy and was shown to contain less than 0.2% free alcohol and less than 2% polar species (HPLC) and an NMR mole ratio of glucose rings to fatty chains of about 1.4.

Example 2–8

The same one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 3.105 moles of the specified alcohol and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57.degree. C. and heating was continued until the slurry had reached 110.degree. C. At this time 3.2 g (0.00345 mole of a commercially available mixture of 50% dinonyinaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in $H_2O$) was added. An aliquot of the neutralized reaction mixture (3.39 g, 1 g dissolved substance) was dissolved in a total volume of 10 ml with 1:1 isopropanol:water. The pH of this solution was 7.8.

The remainder of the reaction mixture was evaporated to a clear melt at 200.degree. C. and 1 mm pressure using a Leybold-Heraeus Distact.™. wiped film evaporator operating at a feed rate of 700 ml/hr.

The residue was analyzed using a combination of gas and liquid chromatographic techniques as well as NMR spectroscopy and was shown to contain less than 0.2% free alcohol and less than 2% polar species (HPLC) and an NMR mole ratio of glucose rings to fatty chains of about 1.4. The hydroxyl value was run on the resultant product and is indicated below.

| Example | Alkyl | OH Value |
|---|---|---|
| 2 | $C_{12}H_{25}$ | 691.9 |
| 3 | $C_{10}H_{21}$ | 741.8 |
| 4 | $C_8H_{17}$ | 795.4 |
| 5 | $C_{14}H_{27}$ | 653.8 |
| 6 | $C_{18}H_{37}$ | 584.4 |
| 7 | $C_{18}H_{35}$ | 586.7 |
| 8 | $C_{20}H_{42}$ | 555.1 |
| 9 | $C_{22}H_{42}$ | 531.2 |

Silicone Functionalized Alkyl Polyglucoside Surfactants

There are a number of types of silicone groups that can be introduced into the finished alkyl polyglycoside. These include (a) products in which the value of b is 1 monofunctional, wherein the resulting product is not polymeric (b) products in which the value of b is greater 2 or greater, wherein there will be crosslinking between alkyl polyglucoside groups through the silicone's "b" unit, or (c) products in which the value of c is 1 or greater. These products will have increasing water solubility as the values of "b", x, y and z increase.

It will be clearly understood that the alkyl polyglycosides of the present invention have a number of hydroxyl groups present in the molecule. The number of hydroxyl groups functionalized will have a profound effect upon the degree of increased water solubility of the molecule.

The present invention includes a functionalization of a low number of hydroxyl groups (one per molecule) to a high number (all groups on the molecule). The preferred number to functionalize is an intermediate number of groups (approximately half of the number present).

Silicone Functionalized Alkyl Polyglucoside Phosphates

Epoxy Siicones

Epoxy silicones are items of commerce and are available from Siltech Corporation, Toronto Ontario Canada. They conform to the following structure;

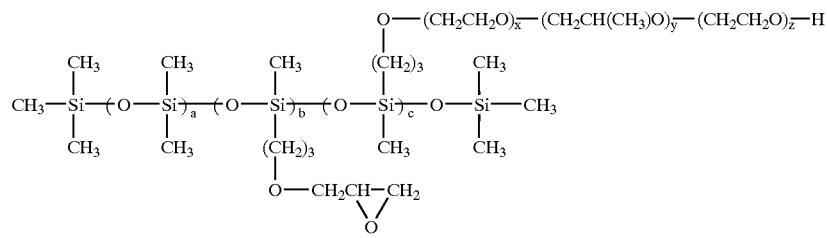

wherein;

a is an integer ranging from 0 to 1,000;

b is an integer :ranging from 1 to 20;

c is an integer ranging from 0 to 20;

x, y and z are each integers independently ranging from 0 to 20.

Epoxy Silicones

| Example | a | b | c | x | y | z |
|---|---|---|---|---|---|---|
| 10 | 0 | 1 | 0 | 0 | 0 | 0 |
| 11 | 5 | 2 | 2 | 5 | 0 | 0 |
| 12 | 10 | 5 | 4 | 0 | 10 | 0 |
| 13 | 15 | 8 | 4 | 0 | 5 | 8 |
| 14 | 20 | 10 | 5 | 10 | 11 | 10 |
| 15 | 50 | 10 | 5 | 10 | 0 | 0 |
| 16 | 100 | 2 | 8 | 10 | 2 | 5 |
| 17 | 200 | 5 | 10 | 11 | 9 | 10 |
| 18 | 500 | 8 | 15 | 14 | 0 | 0 |
| 19 | 1000 | 20 | 20 | 20 | 20 | 20 |

General Procedure. To a flask equipped with agitation, heat, thermometer and nitrogen sparge is added the specified amount of the specified alkyl polyglucoside (examples 1–9) and enough water to make the final product have a solids of 35% by weight. The alkyl polyglucoside is heated to melt. Next, the specified amount of epoxy reacant (examples 10–19) is added under good agitation and nitrogen sparge. Next is added 0.5% sodium methylate. The % is by weight and is based upon the total amount of all materials reacted. Nitrogen sparge is simply nitrogen bubbled through the liquid contents of the flask. This keeps the color light, minimizing oxidation and color formation. The reaction mass is heated to 90–100° C., and is held for 5–8 hours. Testing for loss of the epoxy group follows the reaction progress. Once the theoretical value is reached, the reaction is terminated and the product is used without additional purification.

| | Alkyl Polyglucoside | | Epoxy Silicone | | Water |
|---|---|---|---|---|---|
| Examples | Example | Grams | Example | Grams | Grams |
| 20 | 1 | 446.0 | 10 | 348.0 | 1475.0 |
| 21 | 2 | 416.0 | 11 | 768.0 | 2199.0 |
| 22 | 3 | 388.0 | 12 | 2732.4 | 5795.0 |
| 23 | 4 | 472.0 | 13 | 1419.5 | 3513.0 |
| 24 | 5 | 528.0 | 14 | 1155.7 | 3127.0 |
| 25 | 6 | 526.0 | 15 | 2500.0 | 5672.0 |
| 26 | 7 | 554.0 | 16 | 14961.0 | 28866.0 |

-continued

| | Alkyl Polyglucoside | | Epoxy Silicone | | Water |
|---|---|---|---|---|---|
| Examples | Example | Grams | Example | Grams | Grams |
| 27 | 8 | 582.0 | 17 | 12566.0 | 24470.0 |
| 28 | 9 | 610.0 | 18 | 6176.0 | 12298.0 |
| 29 | 1 | 446.0 | 19 | 6925.0 | 13689.0 |

Applications Examples

The compounds of the present invention are used without any additional purification. There are a variety of compounds that can be used in many different applications. The common property is the silicone slip and lubrication properties.

When the % by weight of the molecule that is made up of polyoxyalkylene is over 50% the products are water soluble. They are substantivve to and provide conditrioning effects to hair skin and fiber.

When the % by weight of silicone in moecule is high the molecules are water insoluble and the products are good fiber lburicants. These materials are also good pigment dispersants.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A silicone alkyl polyglucoside composition conforming to the following structure:

(a)

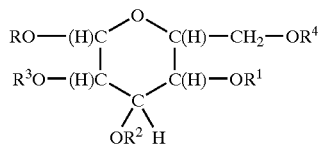

wherein;

R is alkyl having 8 to 22 carbon atoms;

$R^1$, $R^2$, $R^3$, and $R^4$ are independently selected from the group consisting of

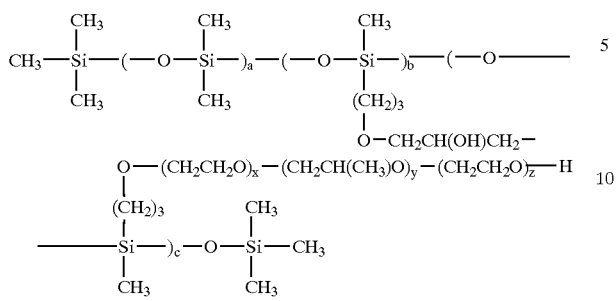

and H, with the proviso that $R^1$, $R^2$, $R^3$, and $R^4$ are not all H;

a is an integer ranging from 0 to 1,000;

b is an integer ranging from 1 to 20;

c is an integer ranging from 0 to 20;

x, y and z are each integers independently ranging from 0 to 20;

and (b)

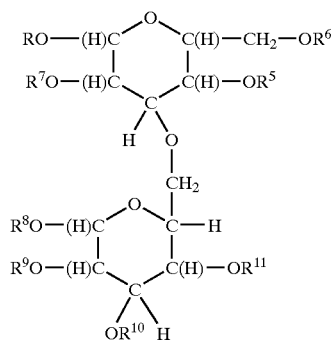

wherein;

R is alkyl having 8 to 22 carbon atoms;

$R^5$, $R^6$, $R^7$, $R^8$; $R^9$ and $R^{10}$ are independently selected from the group consisting of

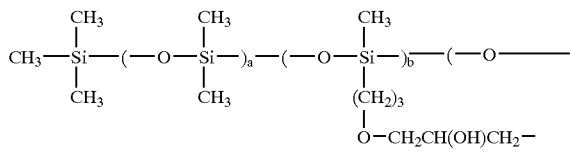

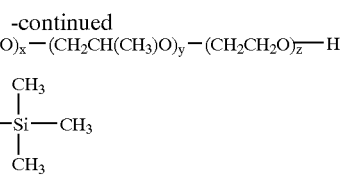

and H, with the proviso that $R^5$, $R^6$, $R^7$, $R^8$, $R^9$ and $R^{10}$ are not all H, a is an integer ranging from 0 to 1,000;

b is an integer ranging from 1 to 20;

c is an integer ranging from 0 to 20;

x, y and z are each integers independently ranging from 0 to 20.

2. A silicone alkyl polyglucoside composition of claim 1 wherein c is 0.

3. A silicone alkyl polyglucoside composition of claim 1 wherein b is 1.

4. A silicone alkyl polyglucoside composition of claim 1 wherein b ranges from 2 to 10.

5. A silicone alkyl polyglucoside composition of claim 1 wherein c ranges from 2 to 10.

6. A silicone alkyl polyglucoside composition of claim 1 wherein R is $C_{12}H_{25}$.

7. A silicone alkyl polyglucoside composition of claim 1 wherein R is $C_{10}H_{21}$.

8. A silicone alkyl polyglucoside composition of claim 1 wherein R is $C_8H_{17}$.

9. A silicone alkyl polyglucoside composition of claim 1 wherein R is $C_{14}H_{27}$.

10. A silicone alkyl polyglucoside composition of claim 1 wherein R is $C_{18}H_{37}$.

11. A silicone alkyl polyglucoside composition of claim 1 wherein R is $C_{18}H_{35}$.

12. A silicone alkyl polyglucoside composition of claim 1 wherein R is $C_{20}H_{42}$.

13. A silicone alkyl polyglucoside composition of claim 1 wherein $C_{22}H_{42}$.

14. A silicone alkyl polyglucoside composition of claim 1 wherein a is an integer ranging from 1 to 200.

15. A silicone alkyl polyglucoside composition of claim 1 wherein a is 0.

16. A silicone alkyl polyglucoside composition of claim 1 wherein a is an integer ranging from 10 to 20.

17. A silicone alkyl polyglucoside composition of claim 1 wherein a is an integer ranging from 2 to 5.

* * * * *